United States Patent [19]
Sienkowski et al.

[11] Patent Number: 4,602,111
[45] Date of Patent: Jul. 22, 1986

[54] POLYBROMO TERTIARY AMINE

[75] Inventors: Kenneth J. Sienkowski, Downers Grove; Ralph B. Thompson, Oakbrook, both of Ill.

[73] Assignee: PPG Industries, Inc., Pittsburgh, Pa.

[21] Appl. No.: 566,744

[22] Filed: Dec. 29, 1983

Related U.S. Application Data

[63] Continuation-in-part of Ser. No. 422,241, Sep. 23, 1982.

[51] Int. Cl.$^4$ .................. C07C 87/50; C07C 87/54
[52] U.S. Cl. ........................................ 564/433; 523/1; 523/461; 523/508
[58] Field of Search ............... 564/433; 523/461, 508, 523/1

[56] References Cited

U.S. PATENT DOCUMENTS

| | | | |
|---|---|---|---|
| 2,196,719 | 3/1939 | Baird et al. | 260/808 |
| 3,221,013 | 11/1965 | Fields et al. | 260/247.1 |
| 3,317,605 | 5/1967 | Weinstock et al. | 260/576 |
| 3,590,074 | 6/1971 | Heiss et al. | 260/479 |
| 3,769,271 | 10/1973 | Southard | 260/112.5 |
| 4,316,988 | 2/1982 | Clinton et al. | 564/433 |
| 4,326,079 | 4/1982 | Romano et al. | 564/393 |
| 4,395,565 | 7/1983 | Romano et al. | 560/24 |

FOREIGN PATENT DOCUMENTS

| | | |
|---|---|---|
| 882135 | 9/1980 | Belgium . |
| 2348910 | 11/1977 | France . |
| 1019912 | 2/1966 | United Kingdom . |
| 1573651 | 8/1980 | United Kingdom . |
| 2044261 | 10/1980 | United Kingdom . |

OTHER PUBLICATIONS

Yamazaki et al., "The Reaction of Diphenyl Carbonate with Amines and Its Application to Polymer Synthesis", *Journal of Polymer Science*, vol. 17, pp. 835–841, (1979).

*Primary Examiner*—Paul F. Shaver
*Attorney, Agent, or Firm*—George D. Morris

[57] ABSTRACT

N,N-Bis(polybromophenyl)organoamines are useful flame retardants which may be admixed with polymers to impart flame retardancy to the resulting compositions. Examples of such flame retardants include N,N-bis(2,4,6-tribromophenyl)methylamine, N,N-bis(2,4,6-tribromophenyl)ethylamine, N,N-bis(2,4,6-tribromophenyl)-allylamine, and N,N-bis(2,4,6-tribromophenyl)-benzylamine.

24 Claims, No Drawings

POLYBROMO TERTIARY AMINE

CROSS REFERENCE TO RELATED APPLICATION

This application is a continuation-in-part of application Ser. No. 422,241, filed Sept. 23, 1982.

THE INVENTION

The present invention provides compounds which are fire retardant and which are especially useful when in admixture with one or more polymers. Accordingly, the present invention provides compounds represented by the structural formula:

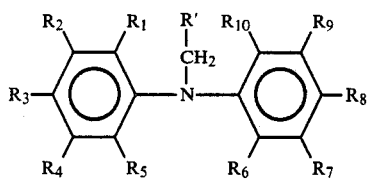

wherein:
a. R' is hydrogen, alkyl, alkenyl, phenylalkyl or phenyl; and
b. $R_1$, $R_2$, $R_3$, $R_4$, $R_5$, $R_6$, $R_7$, $R_8$, $R_9$, and $R_{10}$ are each independently hydrogen or a substituent, with the provisos that at least three of $R_1$, $R_2$, $R_3$, $R_4$, and $R_5$ are bromo and that at least three of $R_6$, $R_7$, $R_8$, $R_9$, and $R_{10}$ are bromo.

Broadly, the minimum of three bromo groups that are on each ring may be located in any of the five available positions. The positions of these bromo groups may be the same as on the other ring, or they may be different. It is preferred, however, that $R_1$ and $R_{10}$ are each bromo. It is especially preferred that $R_1$, $R_3$, $R_5$, $R_6$, $R_8$, and $R_{10}$ are each bromo.

On each ring, there are two positions, each of which may independently be occupied by hydrogen or a substituent. The identity of each substituent which may be located in either or both of these positions may vary widely. Examples of substituents which may be used include halo, nitro, alkyl, alkoxy, alkoxyalkyl, aryloxy, aralkyl, carboxy, acyloxy, aroyloxy, hydroxy, cyano, cycloalkyl, (cycloalkyl)alkyl, acyl, aroyl, mercapto, alkylthio, seleno, alkylseleno, alkenyl, alkadienyl, alkoxycarbonyl, aryloxycarbonyl, and arylalkyloxycarbonyl. The substituents themselves may be substituted, as for example, they may be haloalkyl, halocycloalkyl, nitrobenzyl and the like. Chloro and bromo are typically employed for halo. The alkyl may be straight or branched and usually has from 1 to about 20 carbon atoms. The alkoxy ordinarily has from 1 to about 4 carbon atoms. The alkoxyalkyl generally contains from 1 to 4 carbon atoms in the alkoxy portion and from 1 to about 10 carbon atoms in the alkyl portion. The aryl portion of the aryloxy often contains from 6 to about 10 carbon atoms. The aralkyl often contains from 6 to about 10 carbon atoms in the aryl portion and from 1 to about 10 carbon atoms in the alkyl portion. The acyloxy ordinarily contains from 2 to about 12 carbon atoms. The acyloxy typically contains from 2 to about 7 carbon atoms. The cycloalkyl usually has from about 6 to about 8 carbon atoms. The (cycloalkyl)alkyl generally contains from about 6 to about 8 carbon atoms in the cycloalkyl portion and from 1 to about 10 carbon atoms in the alkyl portion. The aroyl often has from 7 to about 11 carbon atoms. The alkylthio and alkylseleno generally have from 1 to about 4 carbon atoms. The alkenyl typically has from 2 to about 10 carbon atoms. The alkadienyl usually has from about 4 to about 10 carbon atoms. The alkoxycarbonyl ordinarily has from 2 to about 20 carbon atoms. The aryloxycarbonyl generally has from 7 to about 11 carbon atoms. The arylalkyloxycarbonyl usually contains from 6 to about 10 carbon atoms in the aryl portion and from 1 to about 10 carbon atoms in the alkyl portion.

The preferred substituents on the rings are chloro, bromo, or alkyl containing from 1 to about 4 carbon atoms. Bromo is the particularly preferred substituent.

In most cases $R_1$, $R_2$, $R_3$, $R_4$, $R_5$, $R_6$, $R_7$, $R_8$, $R_9$, and $R_{10}$ are each independently hydrogen or bromo with the provisos that at least three of $R_1$, $R_2$, $R_3$, $R_4$, and $R_5$ are bromo and that at least three of $R_6$, $R_7$, $R_8$, $R_9$, and $R_{10}$ are bromo.

In Formula I, R' may be hydrogen, alkyl, alkenyl phenylalkyl, or phenyl. When alkyl is employed, it usually has from 1 to about 9 carbon atoms. Often the alkyl has from 1 to about 5 carbon atoms. Lower alkyl having from 1 to about 3 carbon atoms is preferred. Methyl is especially preferred. When alkenyl is used it generally contains from about 2 to about 5 carbon atoms. Vinyl is preferred. When phenylalkyl is employed the alkyl portion usually contains from 1 to about 3 carbon atoms. The R' groups are usually unsubstituted, although one or more minor substituents which do not render the compound unsuitable for its intended purpose may be present on any of the groups. An example of such a substituted R' group is 1,2-dibromoethyl. The aliphatic groups and the aliphatic portions of the phenylalkyl groups may be straight or branched, but it is preferred they be straight.

Many of the compounds of the present invention may be prepared by reacting an aromatic secondary amine represented by the formula:

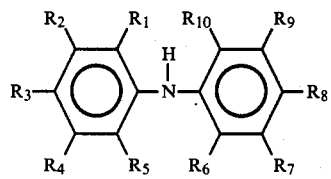

wherein $R_1$, $R_2$, $R_3$, $R_4$, $R_5$, $R_6$, $R_7$, $R_8$, $R_9$, and $R_{10}$ are as previously discussed, with organic carbonate of at least one primary alcohol.

The organic carbonate of at least one primary alcohol used in the method is subject to wide variation. A class of particular importance may be represented by the formula:

wherein R' is as discussed previously in respect of the compound of Formula I, and R'' is alkyl, phenylalkyl or phenyl. When R'' is alkyl, it usually has from 1 to about 10 carbon atoms, often from 1 to about 6 carbon atoms. Lower alkyl having from 1 to about 4 carbon atoms is preferred. Methyl and ethyl are especially preferred. When R'' is phenylalkyl, the alkyl portion usually contains from 1 to about 4 carbon atoms; benzyl is preferred. These groups are usually unsubstituted, although one or more minor substituents which do not render the organic carbonate unsuitable for its intended purpose may be present on any of the groups. The aliphatic groups and the aliphatic portions of the phenylalkyl groups may be straight or branched, but is preferred they be straight. Only one organic carbonate or a plurality of organic carbonates may be used as desired.

Examples of organic carbonates which may be employed include dimethyl carbonate, ethyl methyl carbonate, diethyl carbonate, propyl methyl carbonate, isopropyl methyl carbonate, isopropyl ethyl carbonate, butyl methyl carbonate, secondary-butyl methyl carbonate, isobutyl methyl carbonate, tertiary-butyl methyl carbonate, cyclohexyl methyl carbonate, benzyl methyl carbonate and phenyl methyl carbonate. It is preferred that R' be hydrogen or methyl. The particularly preferred organic carbonates are dimethyl carbonate and diethyl carbonate.

The reaction of aromatic secondary amine and organic carbonate is usually conducted in the liquid phase. It may be carried out batchwise, continuously, semibatchwise or semicontinusously. When the organic carbonate is a liquid under the conditions of the reaction, it often acts as a solvent for the aromatic secondary amine. Typically, but not necessarily, excess organic carbonate is employed and this usually serves to dissolve the aromatic secondary amine throughout the reaction. In many cases, one or more by-products by the reaction, most notably alcohols, also tend to dissolve the aromatic secondary amine. Although extrinsic solvent is not ordinarily employed, it may be used when desired or when necessary to dissolve one or more of the reactants. Examples of suitable extrinsic solvents include methanol, ethanol, acetonitrile, benzene, toluene, dioxane, dimethylformamide and chlorinated solvents such as chloroform, methylene chloride, ethylene chloride, carbon tetrachloride and chlorobenzene. Only one extrinsic solvent or a plurality of extrinsic solvents may be used as desired. For many reactions, extrinsic solvent need not be introduced, and the reaction may be neat.

When extrinsic solvent is used, the weight ratio of extrinsic solvent to the aromatic secondary amine initially present is subject to wide variation. Generally, the amount of solvent should be sufficient to dissolve the reactants at the reaction temperature. The weight ratio of extrinsic solvent, when used, to the aromatic secondary amine initially present is usually in the range of from about 0.01:1 to about 20:1. From about 0.1:1 to about 5:1 is preferred.

The molar ratio of the organic carbonate to the aromatic secondary amine initially present is subject to wide variation but usually it is in the range of from about 0.9:1 to about 100:1. Often it is in the range of from about 1:1 to about 50:1. Preferably the molar ratio is in the range of from about 2:1 to about 25:1.

The temperatures at which the reaction is conducted may vary widely, but ordinarily they are in the range of from about 160° C. to about 240° C. Preferably the temperatures are in the range of from about 180° C. to about 210° C.

The pressures at which the reaction is conducted are similarly susceptible to wide variation. Atmospheric and superatmospheric pressures are generally employed, although lesser pressures may sometimes be used. Generally the pressure is in the range of from about zero to about 5000 kilopascals, gauge, but higher pressures may be used. Preferably the pressure is in the range of from about 500 to about 2000 kilopascals, gauge.

The reaction may be conducted in the presence of catalyst, although in many instances the use of catalyst is not needed. Exemplary catalysts which may be used include nitrogen-containing heterocyclic catalysts such as pyridine, 4-(dimethylamino)pyridine, imidazole, 2,6-lutidine and 2,4,6-collidine. Only a single catalyst or a mixture of catalysts may be used where desired. The preferred catalyst is 4-(dimethylamino)pyridine.

The equivalent ratio of the catalyst, when used, to the aromatic secondary amine initially present may vary widely but usually it is in the range of from about 0.005:1 to about 0.5:1. It is preferred that the equivalent ratio be in the range of from about 0.01:1 to about 0.2:1.

A preferred embodiment of the foregoing method of preparation is the method for alkylating aromatic secondary amine comprising reacting the amine with dialkyl carbonate in which at least one of the alkyl groups of the dialkyl carbonate is unsubstituted methyl or is an alkyl group having at least two carbon atoms wherein the number one carbon atom of the alkyl group is attached to two hydrogen atoms, to produce tertiary amine.

The alkyl groups of the dialkyl carbonate used in this embodiment may be the same or different; it is preferred that they be the same. Typically each alkyl group independently contains from 1 to about 10 carbon atoms, often from 1 to about 6 carbon atoms. Lower alkyl having from 1 to about 4 carbon atoms is preferred. Methyl and ethyl are especially preferred. The alkyl groups of the dialkyl carbonate are usually unsubstituted, although either or both may, subject to the conditions of the immediately preceding paragraph, contain minor substituents which do not render the compound unsuitable for its intended purpose. Only one or a mixture of dialkyl carbonates may be used as desired. The preferred dialkyl carbonates are dimethyl carbonate and diethyl carbonate; dimethyl carbonate is particularly preferred.

The above discussion respecting the aromatic secondary amine is applicable to this embodiment.

Many of the compounds of the present invention may also be prepared by reacting an aromatic secondary amine represented by Formula II wherein $R_1$, $R_2$, $R_3$, $R_4$, $R_5$, $R_6$, $R_7$, $R_8$, $R_9$, and $R_{10}$ are as previously discussed, with organic sulfate of at least one primary alcohol.

The organic sulfate of at least one primary alcohol used in the method is subject to wide variation. A class of particular importance may be represented by the formula:

$$R'CH_2OSOCH_2R''' \quad \text{(IV)}$$

wherein R' is as discussed previously and wherein such discussion is also applicable to R'''. R' and R''' may be the same or they may be different.

The earlier discussion respecting the aromatic secondary amine is also applicable to this method.

Examples of organic sulfates which may be employed include dimethyl sulfate, ethyl methyl sulfate, diethyl sulfate, propyl methyl sulfate, butyl methyl sulfate, isobutyl methyl sulfate, diallyl sulfate, and benzyl methyl sulfate. It is preferred that R' be hydrogen or methyl. The particularly preferred organic sulfates are dimethyl sulfate and diethyl sulfate.

The reaction of aromatic secondary amine and organic sulfate is conducted in the presence of a phase-transfer reagent in a polyphase reaction mixture comprising an organic liquid phase and an aqueous liquid phase. In some instances, especially those in which the phase-transfer reagent is essentially insoluble in the liquid phases and/or those in which precipitate is formed, one or more solid phases may also be present. The reaction may be carried out batchwise, continuously, semi-batchwise, or semi-continuously.

The molar ratio of the organic sulfate to the aromatic secondary amine initially present in the reaction mixture is susceptible to wide variation. Usually the molar ratio is in the range of from about 0.9:1 to about 10:1. A molar ratio in the range of from about 1:1 to about 3:1 is preferred.

Extrinsic organic solvent is ordinarily employed in order to dissolve one or more of the organic reactants. Examples of suitable extrinsic organic solvents include benzene, toluene, and chlorinated solvents such as chloroform, methylene chloride, 1,2-dichloroethane, carbon tetrachloride, and chlorobenzene. Only one extrinsic organic solvent or a plurality of extrinsic organic solvents may be used as desired.

The weight ratio of extrinsic organic solvent to the aromatic secondary amine initially present in the reaction mixture is subject to wide variation. Usually, the amount of such solvent is sufficient to at least partially dissolve the organic reactants at the reaction temperature. The weight ratio of extrinisic organic solvent to the aromatic secondary amine initially present in the reaction mixture is usually in the range of from about 0.01:1 to about 20:1. From about 0.1:1 to about 5:1 is preferred.

The aqueous liquid phase comprises water and a water-soluble base such as the alkali metal hydroxides. Typically, the alkali metal hydroxide is sodium hydroxide or potassium hydroxide. Sodium hydroxide is preferred.

The weight ratio of water to the aromatic secondary amine initially present in the reaction mixture may be widely varied. It is usually in the range of from about 0.01:1 to 20:1. From about 0.1:1 to about 5:1 is preferred.

The molar ratio of water-soluble base to the aromatic secondary amine initially present in the reaction mixture may also be widely varied. Typically it is in the range of from about 1:1 to about 30:1. From about 2:1 to about 10:1 is preferred.

The reaction is conducted in the presence of phase-transfer reagent. Exemplary phase-transfer reagents which may be used include quaternary ammonium salts, quaternary phosphonium salts crown ethers, silacrown ethers, and poly(glycol ethers).

The quaternary ammonium salts are usually, but not necessarily, quaternary ammonium halides. Of these, the quaternary ammonium chlorides are preferred. Exemplarily quaternary ammonium salts include benzyltrimethylammonium chloride, benzyltriethylammonium chloride, methyltrioctylammonium bromide, methyltrioctylammonium chloride, methyltributylammonium chloride, (tetradecyl)trimethylammonium bromide, phenyltrimethylammonium bromide, phenyltrimethylammonium chloride, tetrabutylammonium chloride, tetrabutylammonium iodide, tetrabutylammonium hydrogen sulfate, tetraethylammonium bromide, tetraethylammonium chloride, and tetramethylammonium chloride. Methyltrioctylammonium chloride is preferred. Only one quaternary ammonium salt or a mixture of quaternary ammonium salts may be used.

The quaternary phosphonium salts are usually, but not necessarily, quaternary phosphonium halides. Of these, the quaternary phosphonium chlorides are preferred. Examples of quaternary phosphonium salts include tetrabutylphosphonium bromide, (hexadecyl)trimethylphosphonium chloride, benzyltriphenylphosphonium chloride, benzyltriethylphosphonium chloride, butyltriphenylphosphonium bromide, benzyltriphenylphosphonium chloride, ethyltriphenylphosphonium bromide, (methoxymethyl)triphenylphosphonium chloride, methyltriphenylphosphonium bromide, and propyltriphenylphosphonium bromide. Only one quaternary phosphonium salt or a mixture of quaternary phosphonium salts may be used.

Crown ethers and silacrown ethers are known phase-transfer reagents which have been employed for various reactions. See, for example, U.S. Pat. Nos. 3,562,295; 3,686,225; and 3,687,978; and Gokel and Durst, "Principles and Synthetic Applications in Crown Ether Chemistry", *Synthesis,* March 1976, pages 168–184; Starks and Liotta, *Phase Transfer Catalysts-Principles and Techniques,* Academic Press, New York, pages 77–90 (1978); Arkles et al, "Silacrowns: Phase-Transfer Catalysts", *Organometallics,* Vol. 2, No. 3, pages 454–457 (1983); and *Product Data Sheet, Silanes for Phase Transfer Catalysis,* Petrarch Systems, Inc., Bristol, Pa., the entire disclosures of which are incorporated herein by reference. Examples of such phase-transfer reagents include 12-crown-4, 15-crown-5, 18-crown-6, benzo-15-crown-5, and 1,1-dimethylsila-14-crown-5. Only one crown ether or silacrown ether or a mixture of such materials may be used.

The poly(glycol ethers) are themselves well known materials of widely varying molecular weights. Often the poly(glycol ethers) are poly(ethylene glycol ethers). Poly(ethylene glycol ether) having a molecular weight of about 600 is preferred. Only one poly(glycol ether) or a mixture of poly(glycol ethers) may be used.

The preferred phase-transfer reagent is methyltrioctylammonium chloride.

The weight ratio of the phase-transfer reagent to the aromatic secondary amine initially present in the reaction mixture may vary widely but usually it is in the range of from about 0.005:1 to about 0.5:1. It is preferred that the weight ratio be in the range of from about 0.03:1 to about 0.1:1.

The temperatures at which the reaction is conducted may vary widely, but ordinarily they are in the range of from about 0° C. to about 200° C. Preferably the temperatures are in the range of from about 20° C. to about 100° C.

The pressures at which the reaction is conducted are similarly susceptible to wide variation. Atmospheric and superatmospheric pressures are generally employed, although lesser pressures may sometimes be used. Generally the pressure is in the range of from about zero to about 3500 kilopascals, gauge, but higher pressures may be used. Preferably the pressure is in the range of from about zero to about 350 kilopascals, gauge.

A preferred embodiment of this method of preparation is the method for alkylating aromatic secondary amine comprising reacting the amine with dialkyl sulfate in which at least one of the alkyl groups of the dialkyl sulfate is unsubstituted methyl or is an alkyl group having at least two carbon atoms wherein the number one carbon atom of the alkyl group is attached to two hydrogen atoms, to produce tertiary amine.

The alkyl groups of the dialkyl sulfate used in this embodiment may be the same or different; it is preferred that they be the same. Typically each alkyl group independently contains from 1 to about 20 carbon atoms, often from 1 to about 10 carbon atoms. Lower alkyl having from 1 to about 4 carbon atoms is preferred. Methyl and ethyl are especially preferred. The alkyl groups of the dialkyl sulfate are usually unsubstituted, although either or both may, subject to the conditions of the immediately preceding paragraph, contain minor substituents which do not render the compound unsuitable for its intended purpose. Only one or a mixture of dialkyl sulfates may be used as desired. The preferred dialkyl sulfates are dimethyl sulfate and diethyl sulfate; dimethyl sulfate is particularly preferred.

The earlier discussion respecting the aromatic secondary amine is also applicable to this embodiment.

The compounds of the present invention may also be prepared by reacting an aromatic secondary amine represented by Formula II wherein $R_1$, $R_2$, $R_3$, $R_4$, $R_5$, $R_6$, $R_7$, $R_8$, $R_9$, and $R_{10}$ are as previously discussed, with an organic halide represented by the formula:

$$R'CH_2X \qquad (V)$$

wherein $R'$ is as discussed previously and X is chloro, bromo, or iodo.

The earlier discussion respecting the aromatic secondary amine is also applicable to this method.

Examples of organic halides which may be employed include methyl bromide, methyl iodide, ethyl bromide, ethyl iodide, butyl bromide, benzyl chloride, benzyl bromide, allyl chloride, allyl bromide, phenethyl bromide, pentabromobenzyl bromide, pentabromophenethyl bromide, and cyclohexylmethyl bromide.

The reaction of aromatic secondary amine and organic halide is conducted in the presence of a phase-transfer reagent in a polyphase reaction mixture comprising an organic liquid phase and an aqueous liquid phase. In some instances, especially those in which the phase transfer reagent is essentially insoluble in the liquid phases, one or more solid phases may also be present. The reaction may be carried out batchwise, continuously, semi-batchwise, or semi-continuously.

The molar ratio of the organic halide to the aromatic secondary amine initially present in the reaction mixture is susceptible to wide variation. Usually the molar ratio is in the range of from about 0.9:1 to about 30:1. A molar ratio in the range of from about 1:1 to about 5:1 is preferred.

Extrinsic organic solvent is ordinarily employed in order to dissolve one or more of the organic reactants. Examples of extrinsic organic solvents and the weight ratio of extrinsic organic solvent to the aromatic secondary amine initially present in the reaction mixture are as discussed previously in respect of the organic sulfate method. Similarly, the previous discussions pertaining to the aqueous liquid phase, the water-soluble base, the phase-transfer reagent, the weight ratio of water to the aromatic secondary amine initially present in the reaction mixture, the molar ratio of water-soluble base to the aromatic secondary amine initially present in the reaction mixture, the weight ratio of the phase-transfer reagent to the aromatic secondary amine initially present in the reaction mixture, and the pressures at which the reaction is conducted, are applicable to this organic halide method as well as to the organic sulfate method.

The temperatures at which the reaction is conducted may vary widely, but ordinarily they are in the range of from about 0° C. to about 200° C. Preferably the temperatures are in the range of from about 50° C. to about 150° C.

Following preparation, the polybromo tertiary amine may be recovered from the reaction mixture by any of the various techniques known to the art. Precipitation, crystallization, filtration, and drying are techniques which are frequently employed.

The polybromo tertiary amine of the invention may be incorporated with polymer or polymer-containing composition to provide a composition having greater fire retardancy than in the absence of the polybromo tertiary amine. The individual polybromo tertiary amines of the invention will be more effective with some polymers than with others, but in most cases the desired effect can be obtained by proper adjustment of the polybromo tertiary amine concentration in the composition. The polymer may be flammable or non-flammable, but usually it is flammable. Typically the polymer is thermoplastic, but it may be thermosetting. The polymer may be a homopolymer, a copolymer, a terpolymer, an interpolymer, or a mixture of polymers. Examples of polymers in which the polybromo tertiary amine of the invention may be used include acrylonitrile-butadiene-styrene interpolymer or graft polymer, polystyrene, high density polyethylene, low density polyethylene, polyesters, polyamides, and polycarbonates. The preferred polymers are acrylonitrile-butadiene-styrene graft polymer, polystrene, polyethylene, poly(butylene terephthalate), and aliphatic polyamide. The preferred aliphatic polyamides are poly($\epsilon$-caprolactam) and poly(hexamethylene adipamide).

The amount of the polybromo tertiary amine which is present in compositions of the invention is subject to wide variation. Such polybromo tertiary amine is ordinarily present in an amount in the range of from about 0.1 percent to about 40 percent by weight of the polymer. From about 2 percent to about 25 percent by weight is preferred. Only one polybromo tertiary amine or a plurality of polybromo tertiary amines may be used.

One or more other materials which increase fire retardancy may optionally also be present in the composition. Examples of such materials include zinc oxide, zinc borate, boric acid, borax, ferric oxide, antimony trioxide and antimony pentoxide. Antimony trioxide is preferred. The amounts of these materials are also subject to wide variation. When used, they are usually present in the composition of the invention in an amount in the range of from about 0.1 to about 15 percent by weight. An amount in the range of from about 1 percent to about 10 percent by weight is preferred.

The compositions of the invention may optionally contain plasticizers, pigments, dyes, tints, antioxidants, visible light stabilizers, ultraviolet light stabilizers, resinous pigment dispersants or grinding vehicles, and the like.

The listing of optional ingredients discussed above is by no means exhaustive. These and other ingredients may be employed in their customary amounts for their customary purposes so long as they do not seriously interfere with good polymer formulating practice.

The compositions of the invention are usually prepared by simply admixing the various ingredients. This may be accomplished in many instances by milling. If the polymer and the polybromo tertiary amine are both soluble in solvent, they may be dissolved and mixed, and the polymer mixture recovered by removal of the solvent. Most often, the materials are admixed while the polymer is in the form of a melt. In those instances where the polybromo tertiary amine is introduced as a solid, it is preferred that it be micronized or otherwise reduced in size to about 6 micrometers or less prior to the introduction.

The compositions of the invention have fire retardant characteristics and find many uses. Typically, they may be extruded into fibers, films or other shapes, or molded, shaped or formed into substantially any form. Many of the compositions may be used as adhesives. Where the polymers of the composition are soluble in solvent or are dispersible in liquid nonsolvents such as water, organic nonsolvent or miscible systems of water and organic liquid, the composition may be employed in coating compositions. In the illustrative examples which follow, all parts are parts by weight and all percentages are percentages by weight unless otherwise specified.

EXAMPLE I

A one-liter reactor equipped with an agitator, an automatic temperature controller, a pressure gauge and an electric heating mantle was charged with 50 grams of bis(2,4,6-tribromophenyl)amine and 160 grams of dimethyl carbonate. The reactor was sealed and heated while the contents were agitated. The temperatures and pressures at various times after heating was begun are shown in Table 1.

TABLE 1

| Time, Hours:Minutes | Temperature, °C. | Pressure, Kilopascals Gauge |
|---|---|---|
| 0:0 | Room | 0 |
| 0:10 | 55 | 138 |
| 0:50 | 160 | 827 |
| 1:20 | 180 | 1172 |
| 2:40 | 180 | 1241 |
| 3:50 | 180 | 1379 |
| 4:25 | 180 | 1448 |
| 4:50 | 180 | 1517 |

Four hours and fifty minutes after heating was begun, heating was discontinued and the reactor was allowed to cool. Twenty-three hours and thirty-five minutes after heating was begun, the temperature and pressure were observed to be room temperature and 207 kilopascals gauge, respectively. A sample of gas taken from the reactor was analyzed and found to contain carbon dioxide. The pressure was reduced to ambient and the reactor was found to contain 198.0 grams of liquid. After removal of dimethyl carbonate and methanol by vacuum stripping, analysis of the solidified residue by liquid chromatography showed it to contain 63 area percent N,N-bis(2,4,6-tribromophenyl)methylamine and 36 area percent bis(2,4,6-tribromophenyl)amine.

EXAMPLE II

The reactor of Example I was charged with 50 grams of bis(2,4,6-tribromophenyl)amine and 160 grams of dimethyl carbonate. The reactor was sealed and heated while the contents were agitated. The temperatures and pressures at various times after heating was begun are shown in Table 2.

TABLE 2

| Time, Hours:Minutes | Temperature, °C. | Pressure, Kilopascals Gauge |
|---|---|---|
| 0:0 | Room | 0 |
| 0:35 | 185 | 1517 |
| 1:35 | 195 | 1724 |
| 2:43 | 195 | 2068 |
| 3:05 | 195 | 2206 |
| 4:05 | 195 | 2413 |
| 4:50 | 195 | 2482 |

Four hours and fifty minutes after heating was begun, heating was discontinued and the reactor was allowed to cool. Twenty-three hours and twenty minutes after heating was begun, the temperature and pressure were observed to be room temperature and 276 kilopascals gauge, respectively. The pressure was reduced to ambient and the reactor was found to contain 195 grams of liquid. After removal of dimethyl carbonate and methanol by vacuum stripping, analysis of the solidified residue liquid chromatography showed it to contain 87 area percent N,N-bis(2,4,6-tribromophenyl)methylamine and 11 area percent bis(2,4,6-tribromophenyl)amine. N,N-bis(2,4,6-tribromophenyl)methylamine is useful as a fire retardant additive for polymers, especially, acrylonitrile-butadiene-styrene interpolymers, high density polyethylene, and polyesters such as poly(butylene terephthalate).

EXAMPLE III

A 3-necked reaction flask equipped with an agitator, a thermometer, a reflux condenser and an electric heating mantle was charged with 50 grams of bis(2,4,6-tribromophenyl)amine 300 milliliters of 1,2-dichloroethane, 100 milliliters of 50% aqueous sodium hydroxide solution and 11.4 milliliters of dimethyl sulfate. The reaction flask was heated while the contents were agitated. The temperatures at various times after heating was begun are shown in Table 3.

TABLE 3

| Time, Hours:Minutes | Temperature, °C. | Remarks |
|---|---|---|
| 0:00 | Ambient | Heating begun. |
| 0:20 | 75 | |
| 0:45 | 80 | Added dropwise 3.4 grams of methyltrioctylammonium chloride (Aliquot 336; from Aldrich Chemical Co.) |
| 2:45 | 75 | |
| 4:30 | 75 | |
| 5:40 | 75 | The reaction was discontinued. |

The reaction mixture was filtered and the solids were washed with one liter of water, filtered, washed with methanol, filtered, washed with acetone, filtered, and dried. Liquid chromatography showed the resulting product to contain 96 area percent N,N-bis(2,4,6-tribromophenyl)methylamine.

EXAMPLE IV

A 500 milliliter, 3-necked reaction flask equipped as in Example III was charged with 15.0 grams of bis(2,4,6-tribromophenyl)amine, 150 milliliters of 1,2-dichloroethane, 115 milliliters of 50% aqueous sodium hydroxide solution, 4.5 grams of dimethyl sulfate, and 0.8 gram of benzyltriethylammonium chloride. The reaction flask was heated while the contents were agitated. The temperatures at various times after heating was begun are shown in Table 4.

TABLE 4

| Time, Hours:Minutes | Temperature, °C. | Remarks |
|---|---|---|
| 0:00 | Ambient | Heating begun. |
| 0:14 | 45 | |
| 0:21 | 62 | |
| 0:27 | 79 | |
| 0:42 | 78 | |
| 0:52 | 65 | |
| 0:55 | 67 | |
| 1:10 | 70 | |
| 2:32 | 75 | |
| 4:19 | 76 | |
| 5:24 | 76 | |
| 5:52 | 76 | |
| 6:27 | 75 | |
| 7:02 | 75 | Heating discontinued. |

After standing overnight, the reaction mixture was poured into a beaker and 500 milliliters of water was added. The aqueous layer was removed by decantation. To the organic liquid and solid precipitate which remained was added methanol. The solids were removed by filtration, washed with 500 milliliters of 6% aqueous ammonium hydroxide solution, and dried in air. The resulting product weighed 13.7 grams and melted in the range of from 184° C. to 188° C. Liquid chromatography showed the product to contain greater than 98 area percent N,N-bis(2,4,6-tribromophenyl)methylamine. The product was analyzed from bromine. Found: 73.46%, 72.86%, 72.78% Br.

EXAMPLE V

A 1-liter, 4-necked reaction flask equipped as in Example III was charged with 100 grams of bis(2,4,6-tribromophenyl)amine, 300 milliliters of toluene, 200 milliliters of 50% aqueous sodium hydroxide solution, 30 milliliters of diethyl sulfate, and 6.4 grams of methyltrioctylammonium chloride (Aliquot 336). The reaction flask was heated while the contents were agitated. The temperatures at various times after heating was begun are shown in Table 5.

TABLE 5

| Time, Hours:Minutes | Temperature, °C. | Remarks |
|---|---|---|
| 0:00 | 24 | Heating begun. |
| 0:06 | 30 | |
| 0:10 | 37 | |
| 0:12 | 40 | |
| 0:16 | 45 | |
| 0:20 | 50 | |
| 0:23 | 54 | |
| 0:25 | 57 | |
| 0:28 | 60 | |
| 0:34 | 70 | |
| 0:41 | 80 | |
| 0:46 | 90 | |
| 0:50 | 91 | |
| 0:53 | 90 | |
| 0:58 | 85 | |
| 1:05 | 80 | |
| 1:10 | 78 | |
| 1:18 | 85 | |
| 1:40 | 72 | Heating discontinued. |

After the reaction mixture had cooled for 35 minutes, 250 milliliters of water and 3 milliliters of concentrated ammonium hydroxide were added. The reaction flask was then placed in an ice bath and allowed to stand overnight. The reaction mixture was filtered to remove the solids and the two-phase filtrate was set aside. The solids were washed, first with 250 milliliters of water and then with 300 milliliters of methanol, and then dried. The two-phase filtrate was phase separated. Methanol was added to the organic phase and additional solids were formed. These solids were removed by filtration and dried. The two crops of dried solids were admixed to form the product, which melted at 165° C. Liquid chromatography showed the product to contain 97.0 area percent N,N-bis(2,4,6-tribromophenyl)ethylamine. The product was analyzed for bromine. Found: 70.91%, 70.49% Br. Thermogravimetric analysis of the product in a flowing nitrogen atmosphere at a heating rate of 10° C./minute indicated a 1 percent weight loss at 240° C., a 5 percent weight loss at 278° C. and a 10 percent weight loss at 296° C. The melting point as determined by differential scanning calorimetry was 150° C. with decomposition at 328° C.

EXAMPLE VI

A 1-liter, 4-necked reaction flask equipped as in Example III was charged with 76.9 grams of bis(2,4,6-tribromophenyl)amine, 9.1 grams of methyltrioctylammonium chloride (Aliquot 336), 38.5 grams of 50% aqueous sodium hydroxide solution, 49.8 grams of benzyl chloride, and 500 milliliters of toluene. The reaction mixture was slowly heated to 70° C. and held at 70° C. for 5½ hours. Heating was discontinued and the reaction mixture was allowed to stand overnight. The reaction mixture was slowly heated to 70° C. and held at 70° C. for 3¾ hours. Heating was discontinued and the reaction mixture was allowed to stand overnight. The reaction mixture was slowly heated to 70° C. and held at 70° C. for 6¼ hours. At the end of this period 8.1 grams of methyltrioctylammonium chloride (Aliquot 336), 95.2 grams of 50% aqueous sodium hydroxide solution, 50.2 grams of benyzl chloride, and 25 milliliters of toluene were added. The reaction mixture was heated at 70° C. for another hour. Heating was then discontinued and the reaction mixture was allowed to stand overnight. The reaction mixture was slowly heated to 70° C. and held at 70° C. for 7 hours. Heating was discontinued and the reaction mixture was allowed to stand overnight. The reaction mixture was slowly heated to 85° C. and held at 85° C. for 7¼ hours. Heating was discontinued and the reaction mixture was allowed to stand over the weekend. The reaction mixture was slowly heated to 85° C. and held at 85° C. for 6 hours. Heating was discontinued and the reaction mixture was allowed to stand overnight. To the reaction mixture was added 250 milliliters of water. After stirring for 15 minutes, the reaction mixture was filtered to remove solids and the filtrate was placed in a separatory funnel. The aqueous layer was removed and discarded. The organic layer was washed four times with 250 milliliter portions of water. After each washing about 100 milliliters of saturated aqueous ammonium sulfate was added to break the emulsion which formed and the aqueous layer was removed and discarded. The organic layer was then placed in a beaker and 1500 milliliters of methanol was added with stirring. Upon completion of the addition, the mixture was stirred for 1½ hours. The solids were removed by filtration and slurried once on the filter with methanol. After the liquid had been removed by filtration, the solids were dried overnight in an air oven at 100° C. The resulting product weighed 33.0 grams. Infrared spectroscopy and nuclear magnetic resonance spectroscopy showed the product to be a mixture of N,N-bis(2,4,6-tribromophenyl)benzylamine and bis(2,4,6-tribromophenyl)amine. Liquid chromatography showed the product to apparently contain about 59.9 area percent N,N-bis(2,4,6-tribromophenyl)benzylamine, but the separation of peaks was not good enough to obtain an accurate determination.

EXAMPLE VII

A 1-liter, 3-necked reaction flask equipped as in Example III was charged with 76.8 grams of bis(2,4,6-tribromophenyl)amine, 7.7 grams of benzyltriethylammonium chloride, 31.4 grams of 50% aqueous sodium hydroxide solution, 30.8 grams of allyl bromide, and 500 milliliters of 1,2-dichloroethane. The reaction mixture was heated to reflux (about 78° C.) and held at reflux for 6 hours. Heating was discontinued and the reaction mixture was allowed to stand overnight. The next morning 20 grams of coarse-grained charcoal was added and the reaction mixture was stirred at ambient temperature for 15 minutes. The reaction mixture was filtered. The filtrate was placed in a separatory funnel and the aqueous layer was removed. The organic layer was washed four times with 200 milliliter portions of water. After each washing the aqueous layer was removed and discarded. The organic layer was slurried with anhydrous magnesium sulfate for 30 minutes and then filtered. The filtrate was evaporated to dryness in a rotary evaporator. The resulting product, which was the residue remaining in the evaporator, weighed 65.7 grams. Liquid chromatography showed the product to contain about 65 area percent N,N-bis(2,4,6-tribromophenyl)allylamine. Infrared spectroscopy and nuclear magnetic resonance spectroscopy confirmed the structure as that of N,N-bis(2,4,6-tribromophenyl)allylamine. From these spectra, the assay was estimated to be about 80% to about 85% N,N-(2,4,6-tribromophenyl)allylamine with the remainder being essentially bis(2,4,6-tribromophenyl)amine.

EXAMPLE VIII

A 1-liter, 3-necked reaction flask equipped as in Example III was charged with 66.5 grams of bis(2,4,6-tribromophenyl)amine, 8.8 grams of methyltrioctylammonium chloride (Aliquot 336), 35.2 grams of 50% aqueous sodium hydroxide solution, 41.9 grams of allyl bromide, and 500 milliliters of toluene. The reaction mixture was slowly heated to 70° C. while stirring vigorously, and held at 70° C. for 5½ hours. Heating was discontinued and the reaction mixture was allowed to stand over the weekend. The reaction mixture was slowly heated to 70° C. and held at 70° C. for 7 hours. Heating was discontinued and the reaction mixture was allowed to stand overnight. The next morning 250 milliliters of water was added and the reaction mixture was stirred at ambient temperature for 20 minutes. The reaction mixture was placed in a separatory funnel and the aqueous layer was removed and discarded. The organic layer was washed three times with 250 milliliters portions of water. After each washing the aqueous layer was removed and discarded. The organic layer was placed in a beaker and 1500 milliliters of methanol was added while stirring. Upon completion of the addition stirring was continued at ambient temperature for 2½ hours. The solids were removed by filtration and slurried once on the filter with methanol. After the liquid had been removed by filtration, the solids were dried overnight in an air oven at 100° C. The resulting product weighed 56.2 grams. Liquid chromatography showed the product to be essentially pure N,N-bis(2,4,6-tribromophenyl)allylamine. Infrared spectroscopy and nuclear magnetic resonance spectroscopy confirmed the structure as that of N,N-bis(2,4,6-tribromophenyl)allylamine. The product was analyzed for bromine. Found: 69.61%, 69.81% Br. Thermogravimetric analysis of the product in a flowing nitrogen atmosphere at a heating rate of 10° C./minute indicated at 5 percent weight loss at 273° C., a 10 percent weight loss at 287° C., a 20 percent weight loss at 306° C., and a 40 percent weight loss at 325° C. The melting point as determined by differential scanning calorimetry was 143° C. with decomposition at approximately 255° C. to 265° C.

The N,N-bis(2,4,6-tribromophenyl)allylamine can be brominated by general bromination techniques well known to the art to form N,N-bis(2,4,6-tribromophenyl)-2,3-dibromopropylamine.

In Examples IX and X, a series of compositions, each containing an additive to be evaluated, antimony trioxide and polymer, were tested for fire retardance. For each of the compositions tested, polymer was introduced into a mixer and melted. A mixture of the additive to be evaluated and antimony trioxide was added to the melt and the materials were mixed until uniform to produce the composition. After cooling, each composition was heat pressed into sheets which were cut into bars. The bars were tested for flammability in accordance with the procedure of Vertical Burning Test 94, dated Feb. 1, 1974, of Underwriters Laboratories, Inc., and some compositions were tested in accordance with Standard Method of Test for Flammability of Plastics Using the Oxygen Index Method, ASTM Standard Method D 2863-70, American Society for Testing and Materials. The polymers are abbreviated according to the following key:

ABS=acrylonitrile-butadiene-styrene graft polymer
HIPS=high impact polystyrene
PP=polypropylene
HDPE=high density polyethylene
PBT=glass filled poly(butylene terephthalate); 30% glass fibers, 70% resin, by weight.
NYL=poly(ε-caprolactam)

EXAMPLE IX

The additive to be evaluated was N,N-bis(2,4,6-tribromophenyl)methylamine. Thermogravimetric analysis of this material in a flowing nitrogen atmosphere at a heating rate of 10° C./minute indicated a 1 percent weight loss at 227° C., a 5 percent weight loss at 264° C., and an 8 percent weight loss at 277° C. The material was analyzed for bromine. Found: 73.57%, 73.93% Br. The material melted in the range of 187° C. to 188° C. The structure was confirmed as that of N,N-bis(2,4,6-tribromophenyl)methylamine by infrared spectroscopy and nuclear magnetic resonance spectroscopy.

The identities of the polymers, the proportions of the various materials and the results are shown in Table 6.

TABLE 6

| | Proportions, parts by weight | | | Vertical Burning Test UL 94 | | ASTM Method D 2863-70 Oxygen Index, percent $O_2$ by volume |
|---|---|---|---|---|---|---|
| Polymer | Polymer | Additive | Antimony Trioxide | Classification | After Flame Time, seconds | |
| ABS | 100 | 15 | 5 | 94V-2 | 8.7 | 27.0 |
| ABS | 100 | 15 | 5 | 94V-2 | 10.0 | 25.0 |

TABLE 6-continued

| Polymer | Proportions, parts by weight Polymer | Proportions, parts by weight Additive | Proportions, parts by weight Antimony Trioxide | Vertical Burning Test UL 94 Classification | Vertical Burning Test UL 94 After Flame Time, seconds | ASTM Method D 2863-70 Oxygen Index, percent O$_2$ by volume |
|---|---|---|---|---|---|---|
| ABS | 81.1 | 15.27 | 3.60 | 94V-2 | 3.2 | 27.5 |
| HIPS | 100 | 12 | 4 | Fail | >30 | 24.0 |
| PP | 100 | 5 | 2.5 | Fail | >30 | 24.0 |
| HDPE | 100 | 10 | 5 | 94V-2 | 0.3 | 28.5 |
| HDPE | 100 | 8.7 | 2.9 | 94V-2 | 1.4 | NT |
| PBT | 100[1] | 12 | 3 | 94V-2 | 4.8 | NT[2] |

[1] 30 parts glass fibers and 70 parts resin.
[2] NT = Not Tested.

EXAMPLE X

The additive to be evaluated was the product of Example V. The identities of the polymers, the proportions of materials and the results are shown in Table 7.

TABLE 7

| Polymer | Proportions, parts by weight Polymer | Proportions, parts by weight Additive | Proportions, parts by weight Antimony Trioxide | Vertical Burning Test UL 94 Classification | Vertical Burning Test UL 94 After Flame Time, seconds | ASTM Method D 2863-70 Oxygen Index, percent O$_2$ by volume |
|---|---|---|---|---|---|---|
| ABS | 81.1 | 15.3 | 3.6 | 94V-0 | 2.3 | NT[3] |
| HIPS | 100 | 12 | 4 | Fail | >30 | NT |
| PP | 100 | 5 | 2.5 | Fail | >30 | NT |
| HDPE | 100 | 8.7 | 2.9 | 94V-2 | 13.2 | NT |
| PBT | 100[4] | 12 | 3 | 94V-0 | 0.8 | NT |
| NYL | 100 | 30.4 | 7.6 | 94V-0 | 0.6 | NT |

[3] NT = Not Tested.
[4] 30 parts glass fibers and 70 parts resin.

In Examples XI and XII, a series of compositions, each containing an additive to be evaluated, antimony trioxide and polymer, were tested for fire retardance. For each of the compositions tested, polymer was introduced into a mixer and melted. A mixture of the additive to be evaluated and antimony trioxide was added to the melt and the materials were mixed until uniform to produce the composition. After cooling, each composition was chopped into small pieces and extruded into one-eighth inch (3.175 mm) pellets. The pellets were injection molded into bars. The bars were tested for flammability in accordance with the procedure of Vertical Burning Test 94, dated Feb. 1, 1974, of Underwriters Laboratories, Inc. The polymers are abbreviated according to the key given previously.

EXAMPLE XI

The additive to be evaluated was N,N-bis(2,4,6-tribromophenyl)methylamine and the polymer was HDPE. The proportions of materials and the results are shown in Table 8.

TABLE 8

| Polymer | Proportions, parts by weight Additive | Proportions, parts by weight Antimony Trioxide | Vertical Burning Test UL 94 Classification | Vertical Burning Test UL 94 After Flame Time, seconds |
|---|---|---|---|---|
| 100 | 4.5 | 4.5 | Fail | >30 |
| 100 | 6 | 3 | 94V-2 | 5.4 |
| 100 | 6.75 | 2.25 | 94V-2 | 6.7 |
| 100 | 7.2 | 1.8 | 94V-2 | 6.5 |
| 100 | 7.5 | 1.5 | 94V-2 | 7.4 |
| 100 | 7.33 | 3.67 | 94V-2 | 2.7 |
| 100 | 8.25 | 2.75 | 94V-2 | 1.1 |
| 100 | 8.8 | 2.2 | 94V-2 | 3.6 |
| 100 | 9.17 | 1.83 | 94V-2 | 5.2 |

EXAMPLE XII

The additive to be evaluated was N,N-bis(2,4,6-tribromophenyl)methylamine and the polymer was ABS. The proportions of materials and the results are shown in Table 9.

TABLE 9

| Polymer | Proportions, parts by weight Additive | Proportions, parts by weight Antimony Trioxide | Vertical Burning Test UL 94 Classification | Vertical Burning Test UL 94 After Flame Time, seconds |
|---|---|---|---|---|
| 100 | 21.67 | 4.33 | 94V-0 | 1.7 |

EXAMPLE XIII

A composition containing 100 parts of HDPE polymer, 8.25 parts of N,N-bis(2,4,6-tribromophenyl)methylamine, and 2.75 parts of antimony trioxide was tested for physical properties. The HDPE polymer without either of the additives was also tested for physical properties. The results are shown in Table 10.

TABLE 10

| Test | HDPE With Additives | HDPE Without Additives |
|---|---|---|
| Tensile Strength, megapascals | 16.892 | 19.236 |
| Tensile Modulus, megapascals | 758.423 | 958.371 |
| Flexural Strength, megapascals | 22.615 | 26.959 |
| Flexural Modulus, megapascals | 696.370 | 910.108 |
| Notched Izod Impact Strength, newton-meters/meter | 26.156 | 30.960 |
| Heat Distortion Temperature, °C. | 46 | 46 |
| Specific Gravity | 1.026 | 0.95 |
| Melt Index, grams/10 minutes | 17.3 | 14.3 |

EXAMPLE XIV

A composition containing 100 parts of ABS polymer, 21.67 parts of N,N-bis(2,4,6-tribromophenyl)methylamine, and 4.33 parts of antimony trioxide was tested for physical properties. The results are shown in Table 11.

TABLE 11

| Test | ABS With Additives |
|---|---|
| Tensile Strength, megapascals | 40.196 |
| Tensile Modulus, megapascals | 1558.215 |
| Flexural Strength, megapascals | 75.704 |
| Flexural Modulus, megapascals | 2233.901 |
| Notched Izod Impact Strength, newton-meters/meter | 279.704 |
| Heat Distortion Temperature, °C. | 66 |
| Specific Gravity | 1.19 |
| Melt Index, grams/10 minutes | 1.62 |

Although the present invention has been described with reference to specific details of certain embodiments thereof, it is not intended that such details should be regarded as limitations upon the scope of the invention except insofar as they are included in the accompanying claims.

We claim:

1. A compound represented by the structural formula:

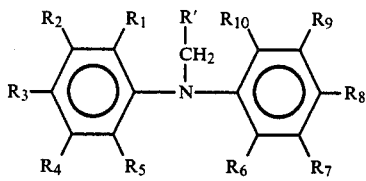

wherein:
a. R' is hydrogen, alkyl, alkenyl, phenylalkyl or phenyl; and
b. $R_1$, $R_2$, $R_3$, $R_4$, $R_5$, $R_6$, $R_7$, $R_8$, $R_9$, and $R_{10}$ are each independently hydrogen or a substituent, with the provisos that at least three of $R_1$, $R_2$, $R_3$, $R_4$, and $R_5$ are bromo and that at least three of $R_6$, $R_7$, $R_8$, $R_9$, and $R_{10}$ are bromo.

2. The compound of claim 1 wherein $R_1$ and $R_{10}$ are each bromo.

3. The compound of claim 1 wherein $R_1$, $R_3$, $R_5$, $R_6$, $R_8$, and $R_{10}$ are each bromo.

4. The compound of claim 1 wherein R' is hydrogen, unsubstituted alkyl having from 1 to about 9 carbon atoms, unsubstituted alkenyl having from 2 to about 5 carbon atoms, unsubstituted phenylalkyl in which the alkyl portion contains from 1 to about 3 carbon atoms, or unsubstituted phenyl.

5. The compound of claim 1 wherein R' is vinyl.

6. The compound of claim 1 which is N,N-bis(2,4,6-tribromophenyl)allylamine.

7. The compound of claim 1 wherein R' is substituted alkyl having from 1 to about 9 carbon atoms, substituted alkenyl having from 2 to about 5 carbon atoms, substituted phenylalkyl in which the alkyl portion contains from 1 to about 3 carbon atoms, or substituted phenyl, and wherein each substituent of said substituted alkyl, said substituted alkenyl, said substituted phenylalkyl, and said substituted phenyl is a minor substituent.

8. The compound of claim 1 wherein R' is hydrogen, alkyl, phenylalkyl, or phenyl.

9. The compound of claim 8 wherein $R_1$ and $R_{10}$ are each bromo.

10. The compound of claim 8 wherein $R_1$, $R_3$, $R_5$, $R_6$, $R_8$, and $R_{10}$ are each bromo.

11. The compound of claim 8 wherein R' is hydrogen, unsubstituted alkyl having from 1 to about 9 carbon atoms, unsubstituted phenylalkyl in which the alkyl portion contains from 1 to about 3 carbon atoms, or unsubstituted phenyl.

12. The compound of claim 8 wherein R' is hydrogen, methyl, or phenyl.

13. The compound of claim 8 wherein R' is substituted alkyl having from 1 to about 9 carbon atoms, substituted phenylalkyl in which the alkyl portion contains from 1 to about 3 carbon atoms, or substituted phenyl, and wherein each substituent of said substituted alkyl, said substituted phenylalkyl, and said substituted phenyl is a minor substituent.

14. The compound of claim 8 wherein $R_1$, $R_2$, $R_3$, $R_4$, $R_5$, $R_6$, $R_7$, $R_8$, $R_9$, and $R_{10}$ are each independently hydrogen or bromo with the provisos that at least three of $R_1$, $R_2$, $R_3$, $R_4$, and $R_5$ are bromo and that at least three of $R_6$, $R_7$, $R_8$, $R_9$, and $R_{10}$ are bromo.

15. The compound of claim 14 wherein R' is hydrogen, unsubstituted alkyl having from 1 to about 9 carbon atoms, unsubstituted phenylalkyl in which the alkyl portion contains from 1 to about 3 carbon atoms, or unsubstituted phenyl.

16. The compound of claim 15 wherein $R_1$ and $R_{10}$ are each bromo.

17. The compound of claim 15 wherein $R_1$, $R_3$, $R_5$, $R_6$, $R_8$, and $R_{10}$ are each bromo.

18. The compound of claim 14 which is N,N-bis(2,4,6-tribromophenyl)ethylamine.

19. The compound of claim 14 which is N,N-bis(2,4,6-tribromophenyl)benzylamine.

20. N,N-bis(2,4,6-tribromophenyl)methylamine.

21. A composition comprising thermoplastic or thermosetting polymer and compound represented by the structural formula:

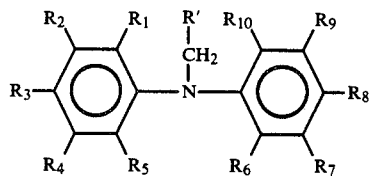

wherein:
a. R' is hydrogen, alkyl, alkenyl, phenylalkyl or phenyl; and
b. $R_1$, $R_2$, $R_3$, $R_4$, $R_5$, $R_6$, $R_7$, $R_8$, $R_9$, and $R_{10}$ are each independently hydrogen or a substituent, with the provisos that at least three of $R_1$, $R_2$, $R_3$, $R_4$, and that $R_5$ are bromo and that at least three of $R_6$, $R_7$, $R_8$, $R_9$, and $R_{10}$ are bromo.

22. The composition of claim 21 wherein said compound is N,N-bis(2,4,6-tribromophenyl)methylamine.

23. The composition of claim 21 wherein said compound is N,N-bis(2,4,6-tribromophenyl)ethylamine.

24. A composition comprising (1) acrylonitrile-butadiene-styrene graft polymer, polyethylene or polyester, and (2) compound represented by the structural formula:

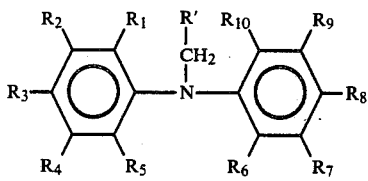

wherein:
a. R' is hydrogen, alkyl, alkenyl, phenylalkyl or phenyl; and
b. $R_1$, $R_2$, $R_3$, $R_4$, $R_5$, $R_6$, $R_7R_8$, $R_9$, and $R_{10}$ are each independently hydrogen or a substituent, with the provisos that at least three of $R_1$, $R_2$, $R_3$, $R_4$ and that $R_5$ are bromo and that at least three of $R_6$, $R_7$, $R_8$, and $R_{10}$ are bromo.

* * * * *